United States Patent [19]
Werge et al.

[11] Patent Number: 5,535,785
[45] Date of Patent: Jul. 16, 1996

[54] LUER-ACTIVATED CHECK VALVE

[75] Inventors: Robert W. Werge, Thompson, Conn.;
Peter N. Kotsifas, Sturbridge, Mass.

[73] Assignee: Nypro, Inc., Clinton, Mass.

[21] Appl. No.: 302,497

[22] Filed: Sep. 8, 1994

[51] Int. Cl.⁶ .............................. F16K 15/14; F16L 29/02
[52] U.S. Cl. ..................... 137/843; 137/903; 251/149.6; 604/249
[58] Field of Search .................................... 137/843, 903; 251/149.1, 149.6, 149.7; 604/83, 249

[56] References Cited

U.S. PATENT DOCUMENTS

| | | |
|---|---|---|
| 3,192,949 | 7/1965 | De See . |
| 3,385,301 | 5/1968 | Harautuneian . |
| 3,499,338 | 2/1969 | Mackal . |
| 3,726,282 | 4/1973 | Patel . |
| 3,831,629 | 8/1974 | Mackal et al. . |
| 4,128,098 | 12/1978 | Bloom et al. . |
| 4,421,296 | 12/1983 | Stephens . |
| 4,602,655 | 7/1986 | Mackal . |
| 4,681,132 | 7/1987 | Lardner . |
| 5,020,562 | 6/1991 | Richmond et al. . |
| 5,064,849 | 11/1991 | Newgard ........................... 251/149.1 X |
| 5,215,538 | 6/1993 | Larkin . |
| 5,289,849 | 3/1994 | Paradis ............................. 251/149.1 X |

*Primary Examiner*—John Rivell
*Attorney, Agent, or Firm*—Bromberg & Sunstein

[57] ABSTRACT

A Luer-activated valve constructed of a single-piece valve element with integral biasing base and ventilated riser disposed within a valve housing providing a valve seat and buttress for the biasing base.

30 Claims, 8 Drawing Sheets

5,535,785

LUER-ACTIVATED CHECK VALVE

BACKGROUND OF THE INVENTION

This invention relates to the control of fluid flow using a check valve responding to fluid injected into the valve by devices such as Luer fittings or cannulas.

Check valves are used extensively in medical applications, such as for intravenous delivery of fluids. In some cases it may be desirable to open the valve by using fluid pressure. In other cases, it may be desirable to open the valve using means other than fluid pressure. Thus, a user may wish to open the valve independently of the presence or extent of fluid pressure, in preparation for anticipated fluid flow. For example, it may be desirable to maintain the valve in its open position for a prescribed interval of time independently of whether fluid flow is present. Another example of a situation in which it is desired that a check valve be open irrespective of fluid pressure is that in which a check valve is connected to a catheter inserted in a patient and it is desired to sample blood or other fluid by opening the check valve and inducing a reverse fluid flow that ordinarily would be checked or stopped by the valve.

In medical applications, it is often desirable to introduce a dosage of drugs into an existing flow of a fluid such as dextrose solution. This is often accomplished by using a syringe with a needle penetrating a rubber seal over a branch of a "Y"-connector. Because of the possibility of needle-induced infections, however, the current trend is to minimize the use of needles and to favor the use of blunt cannulas or Luer fittings.

Prior art check valves providing for the use of wide cannulas or Luer fittings to open the valves have been of the general configuration using a resilient disk situated in a flow channel, supported at the center and pressed at its periphery against a valve seat by the resiliency of the disk and back pressure from downstream fluid. This type of valve is opened by forward pressure applied radially outward of the center but inward of the valve seat either by forward fluid flow or by a separate plunger which acts as an extension of the cannula or Luer fitting.

These valves suffer from a number of disadvantages. First, there is the problem of the plunger collecting debris such as clotted blood that may interfere with the operation of the valve, in a worst case situation applying enough forward bias to crack open the valve unintentionally.

Second, the additional plunger component not only adds to cost in fabrication of the component, but in handling and assembly. The additional component adds the possibility of omission in assembly, resulting in a conventional check valve opened only by forward fluid pressure if the plunger is omitted or in no valve at all if the disk is omitted.

Third, dimensional variations in the multiple cannulas or Luer fittings that may be used with a single valve may result in different operation of the valve. In the worst case, a plunger may be forced against the disk with such force as to damage the disk, and thus the valve.

SUMMARY OF THE INVENTION

Objects of the present invention include the provision of a Luer-activated check valve of simple construction that allows for activation under different pressures and fitting dimensions and avoids the above-noted disadvantages.

In summary, the invention accomplishes these objects by using a one-piece combination valve element, which can be molded of resilient material, combining an annular flange acting as a valve seal, an integral base used to provide a biasing force pressing the valve seal against a valve seat, and an integral, ventilated, riser which acts as a plunger and conduit for fluid injected through a Luer fitting. The valve element is assembled in a housing which provides a valve seat and buttress for the biasing base. The invention may be molded in three parts (two-piece housing) and assembled in a fool-proof manner, since the three components can only be engaged in the correct structural relationship. If the housing is of transparent plastic and the valve element of a high-visibility color, visual inspection is particularly effective.

DETAILED DESCRIPTION OF AN ILLUSTRATIVE EMBODIMENT

Figure 1:
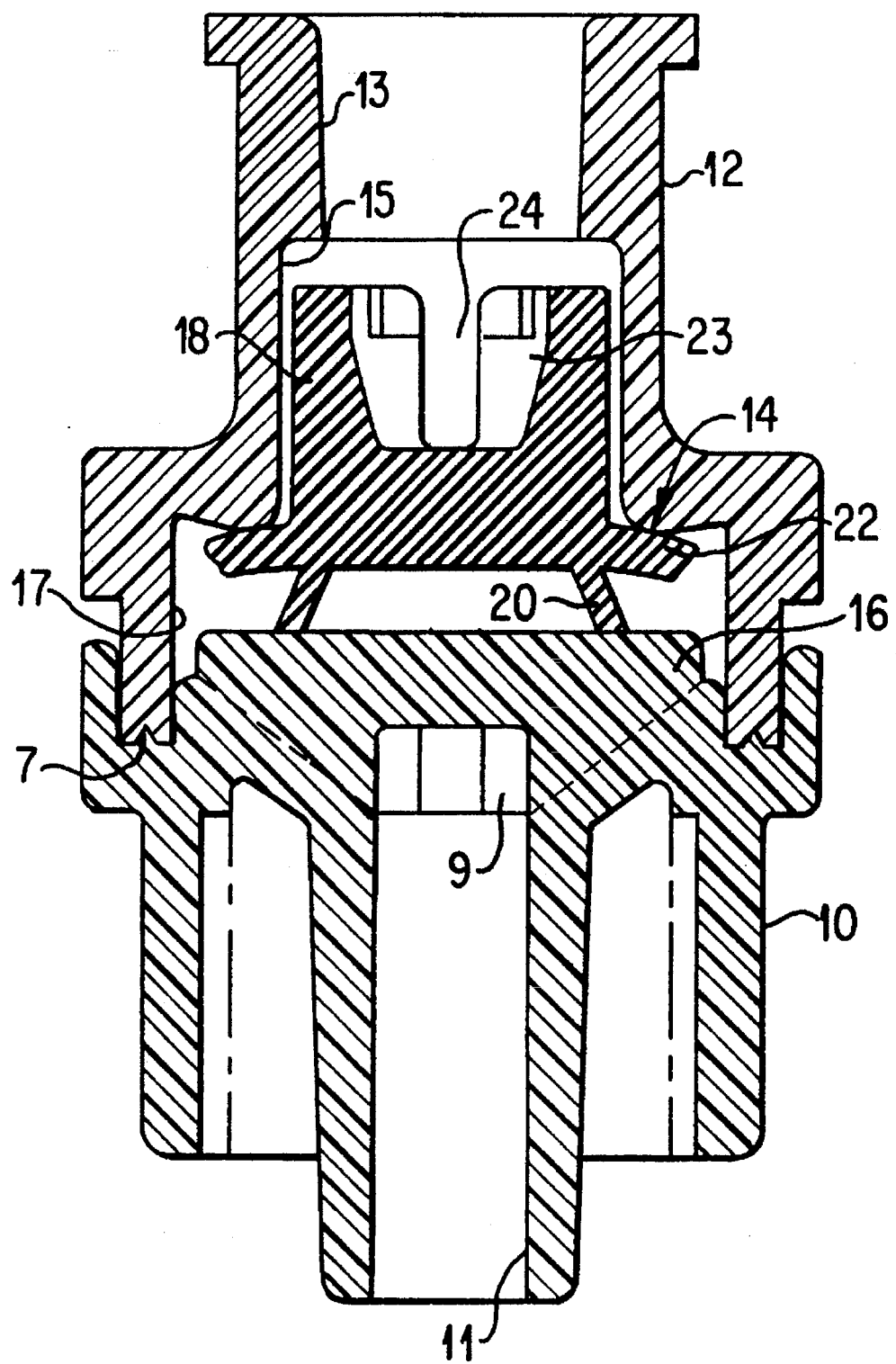
FIG. 1 shows a cross-sectional view of a valve embodying the invention.

An illustrative embodiment of the check valve of the invention is shown in cross-section in FIG. 1. The check valve housing is shown in two parts: a lower housing 10, which is the outlet portion, and an upper housing 12, which is the inlet portion. Axially symmetric (cylindrical) lower housing 10 has tubular outlet flow passage or channel portion 11 which communicates with a wider channel portion 9 (partly obscured by vanes or buttresses 16). Cylindrical upper housing 12 has, from the top or inlet end, channel portion 13, a slightly wider channel portion 15 (the difference provided to entrain valve element 18 and to guide a male Luer fitting), an annular valve seat 14, and a significantly wider channel portion 17 (which communicates with channel portion 9 defined by lower housing 10). With valve element 18 positioned as shown in FIG. 1, lower housing 10 and upper housing 12 are sealed together at 7 by ultrasonic welding.

Hat-shaped valve element 18 is integrally formed of resilient material in the general form of a disk with an annular extension or riser 23 defining a projecting flange 22.

In the embodiment shown in FIG. 1, valve element 18 also has an annular extension or base 20 compressed against buttresses 16 (in an annular region radially inward of the wall defining channel portion 17) which may be further compressed when the valve element is pushed downwardly from above such as by a Luer fitting or wide cannula engaging riser 23 or by downward fluid pressure sufficient to so compress base 20. Riser 23 is positioned with relatively small clearance within the walls defining channel 15 so that fluid may flow between the walls and riser 23 in the open mode, while assuring a proper seal between flange 22 (which may be radially wider than said clearance) and valve seat 14 in the closed mode. (In an alternative embodiment, there may be ribs in channel 17 guiding flange 22 to facilitate centering of valve element 18.) Thus, flange 22 on the valve element 18 normally contacts the valve seat 14 and prevents flow downwardly through the valve except when the valve element 18 is pressed downwardly and the flange 22 is lowered from valve seat 14. So activated, downward fluid flow can then take place from the upper housing 12 through channel portion 13 through slots 24 in riser 23 in channel portion 15, around the flange 22 and between the space between the flange 22 and the valve seat 14, through wider channel portion 17, around the buttresses 16 and then through the lower housing 10 through channel portions 9 and 11.

This construction provides a check valve which prevents fluid flow in the upward direction from the lower housing 10 to upper housing 12, unless the valve is activated or opened by a Luer fitting or wide cannula engaging riser 23 with adequate pressure in the outlet direction. Slot 24 provides both a channel for fluid flow and, aided by an internal taper of riser 23 (shown as castellated or alternating bevels 26 and beveled radially inward projections 27 in FIG. 2), resilient acceptance of Luer fittings and wide cannulas of a range of dimensions with uniform operation of the valve and minimal probability of damage. The riser 23 is preferably dimensioned so that, when a Luer fitting is inserted into the upper housing 12 through channel portion 13, the tip of the Luer fitting will normally engage the inside diameter of the slotted hollow cylinder of the riser 23. Thus, the tip of the Luer fitting will normally tend to widen the slots 24 and separate the two semicylindrical portions of the riser 23 from each other. By providing the riser 23 with such a structure, the valve is provided with the necessary compliance to accommodate Luer fittings of differing dimensions.

In the illustrative embodiment, lower housing 10 and upper housing 12 are injection-molded of relatively hard, transparent plastic. The lower housing 10 is shown as providing a male locking Luer fitting, and the upper housing 12 is shown as providing a female locking Luer fitting. These external configurations of lower housing 10 and upper housing 12 may be varied for connection to other Luer fittings or directly to tubes. Other alternatives may include the provision of integral "Y"- or "T"-style outlet connectors. The difference in external configuration between lower housing 10 and upper housing 12 as shown provides a convenient means for distinguishing between the components during assembly and for indicating the direction of flow in use.

Figure 2:
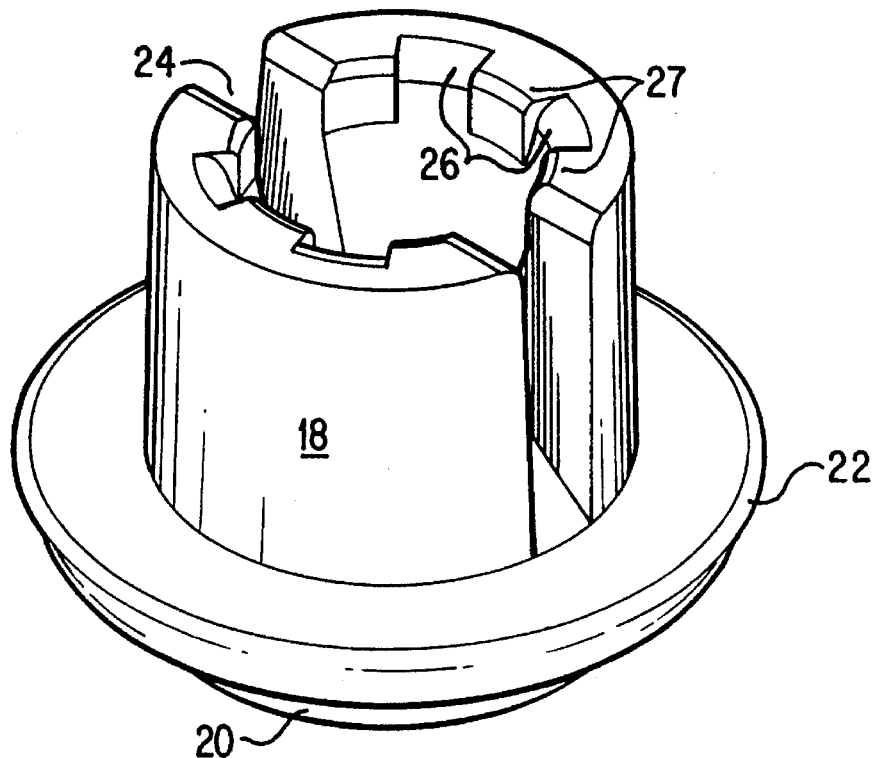
FIG. 2 shows a perspective view of the valve element of FIG. 1.
Figure 3:
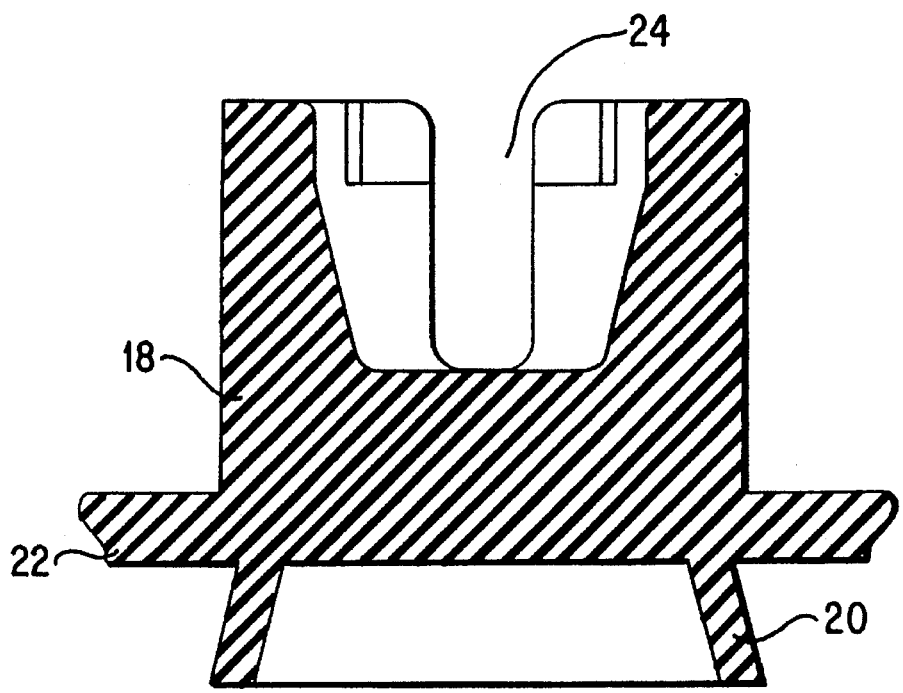
FIG. 3 shows a cross-sectional view of the valve element of FIG. 1.
Figure 3A:
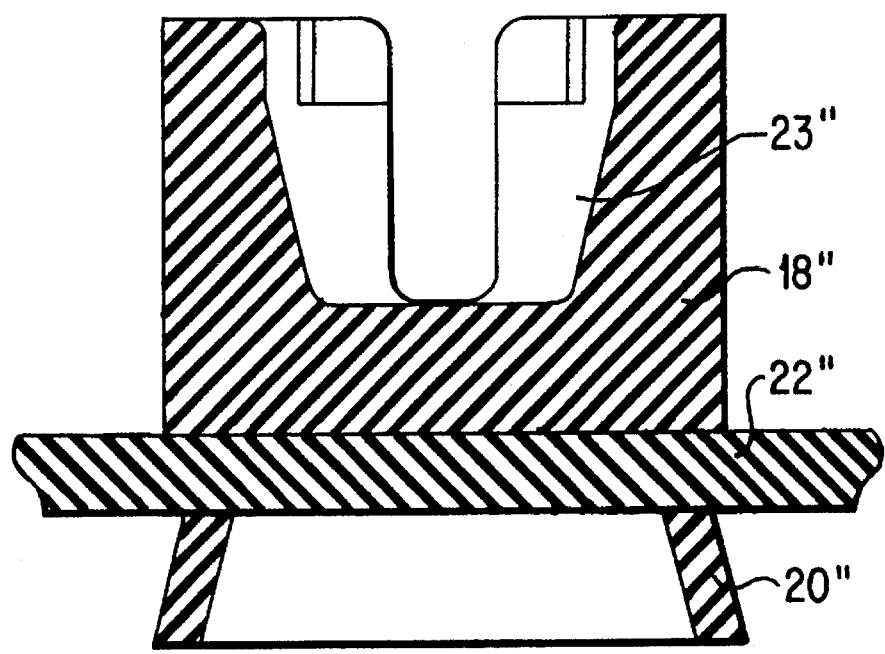
FIG. 3A shows a cross-sectional view of an alternative valve element.
Figure 3B:
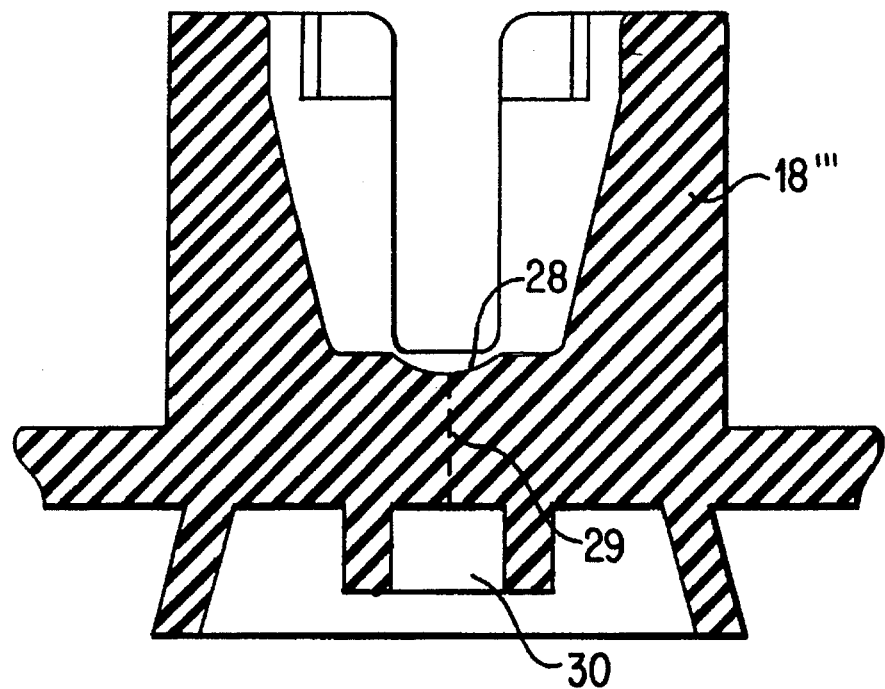
FIG. 3B shows a cross-sectional view of another alternative valve element.

Valve element 18 is molded in a single piece of a resilient material such as an elastomer and is shown in further detail in perspective in FIG. 2 and in cross-section in FIG. 3. In this illustrative embodiment, base 20 is formed as the hollow frustum of a cone; in this configuration, cracking pressure may be varied by varying the angle of the base extension or the length or thickness of the extension. In another embodiment, base 20 may be a cylindrical extension, and cracking pressure varied by varying the axial or radial dimensions. Yet another way of varying cracking pressure is by molding valve element 18 in one piece, but using materials of different resilience in different portions of the valve element, for example, in valve element 18'' of FIG. 3A, the base 20' may be cast with a mix of elastomer resulting in one stiffness, while a disk layer including flange 22'' may be cast with a different mix of elastomer resulting in a different stiffness, and riser 23'' may be cast with yet a different mix of elastomer resulting in yet a different stiffness. In each case, it is advantageous for visual inspection both for quality control and user selection, to color (and color-code for different cracking pressures) the valve element so that it is easily visible through the transparent housing.

Figure 1A:
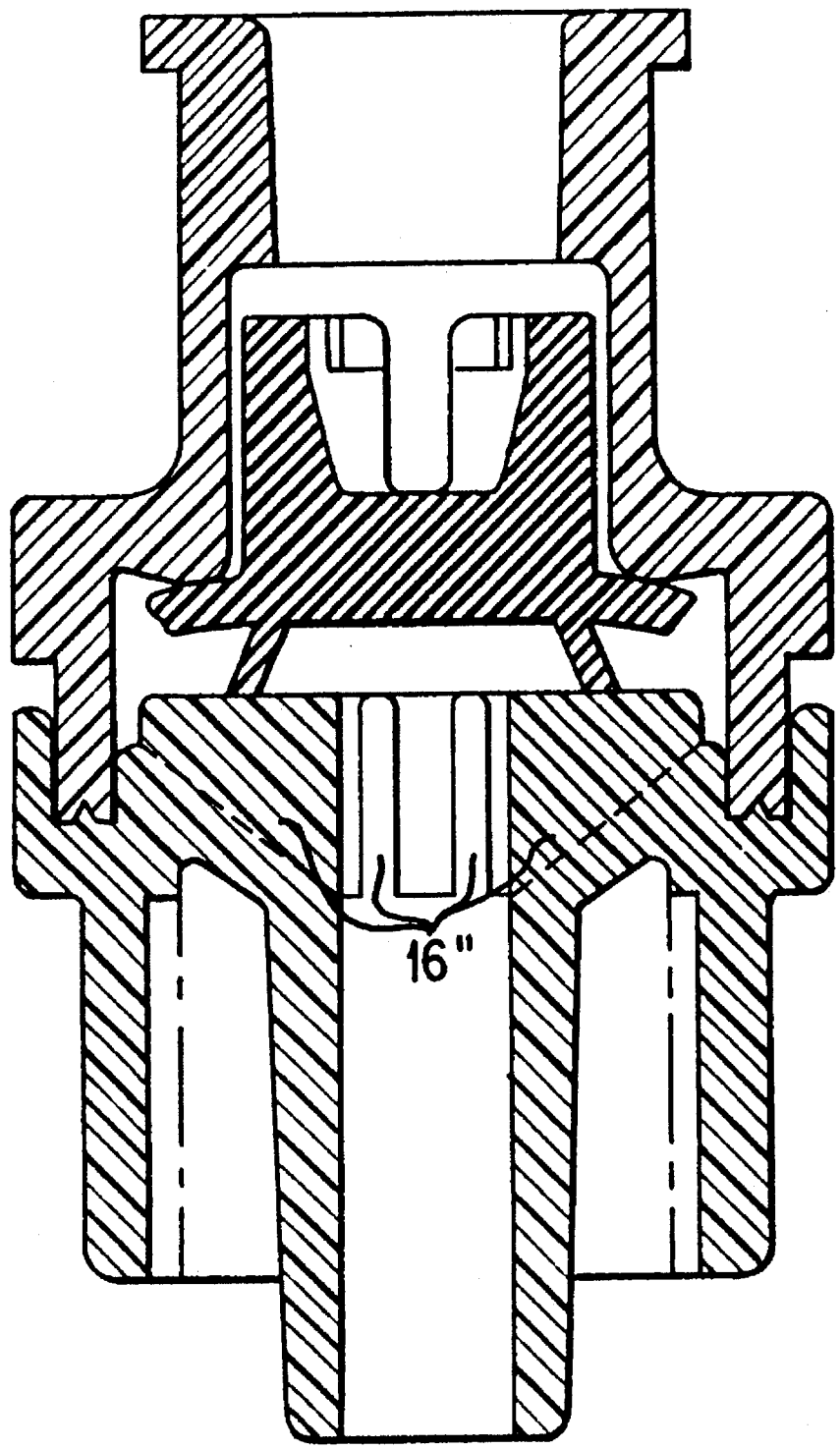
FIG. 1A shows a cross-sectional view of an alternative embodiment of the invention.

Further variations of the illustrative embodiment include its adaptations for use with syringe needles or narrow blunt cannulas. Either may be accommodated by spacing the buttresses 16'' away from the central axis as shown in FIG. 1A. For needles, the center of valve element 18 may made thin enough to facilitate piercing by a needle, but thick enough to prevent fluid flow through the puncture (or to heal if self-healing material is used) and otherwise to allow proper check-valve and Luer-activated operation under normal operating conditions. For blunt cannulas, the center of valve element 18'' may be slit or perforation at 29 to facilitate piercing by the cannula, but thick enough to prevent fluid flow through the slit and otherwise to allow proper check-valve and Luer-activated operation under normal operating conditions. For the cannula embodiment, an additional extension 30 may be provided axially from the central portion of the disk immediately surrounding the slit or perforation 29 to engage the buttresses (appropriately spaced) to prevent opening of the valve during insertion of a cannula. In either the needle or cannula embodiment, the central region of valve element 18'' may be further provided with a taper or indentation 28 toward the center to facilitate positioning a needle or cannula.

Figure 4:
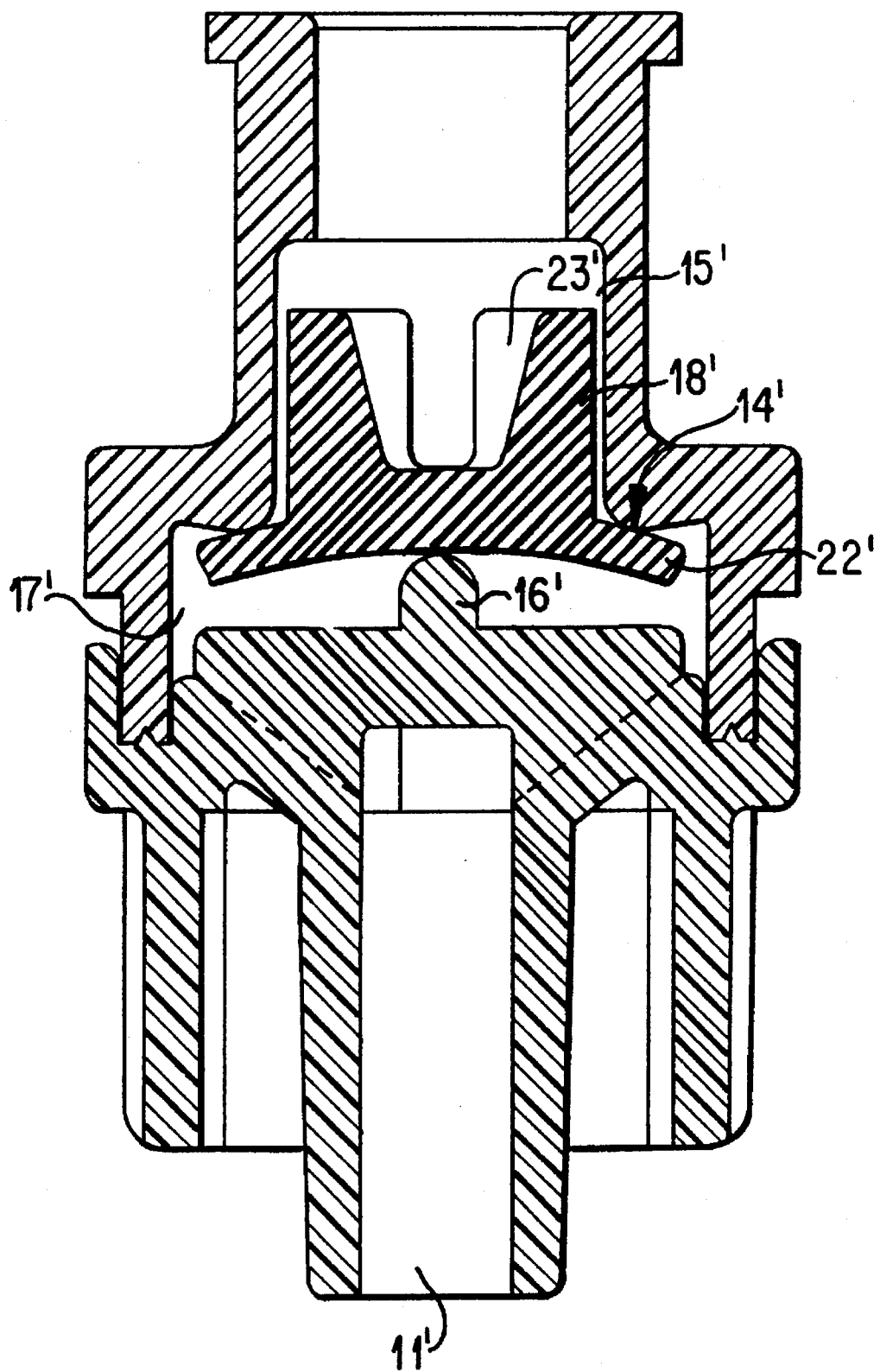
FIG. 4 shows a cross-sectional view of an alternative embodiment of the invention.

An alternative embodiment of the invention is shown in cross-section in FIG. 4. In this embodiment, valve element 18', also hat-shaped and integrally formed of resilient material, comprises a disk defining an annular flange 22' with inlet-end annular axial extension or riser 23', which may have the same variations in configuration as riser 23 in valve element 18 of the embodiment shown in FIG. 1 and described above. Valve element 18', however, does not have the base annular axial extension corresponding to base 20 in valve element 18 in FIG. 1 to provide biasing of the flange against the valve seat. Instead, valve element 18' is biased against valve seat 14' by a central portion of buttress 16' extending axially in the inlet direction (here shown as a single central prong). When inlet pressure is applied by fluid or a male Luer fitting, valve element 18' is moved axially in the outlet direction in channel portion 17' against increasing back pressure provided by the central portion of valve element 18' pressing against buttress extension 16', as well as by any fluid back pressure. With enough forward pressure, flange portion 22' is separated from valve seat 14', allowing fluid communication between channel portions 15', 17' and 11'.

Figure 1B:
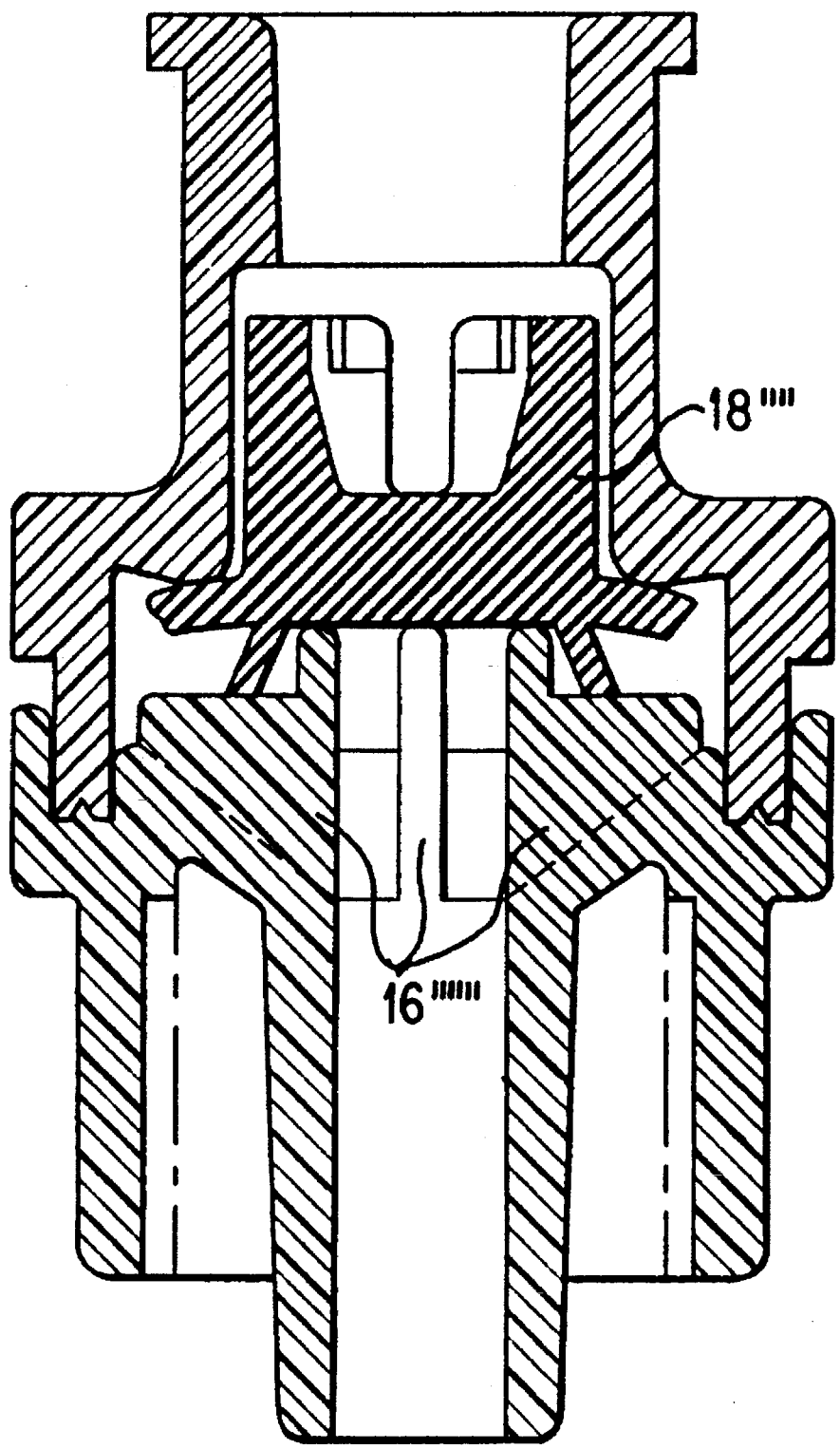
FIG. 1B shows a cross-sectional view of another alternative embodiment of the invention.
Figure 4A:
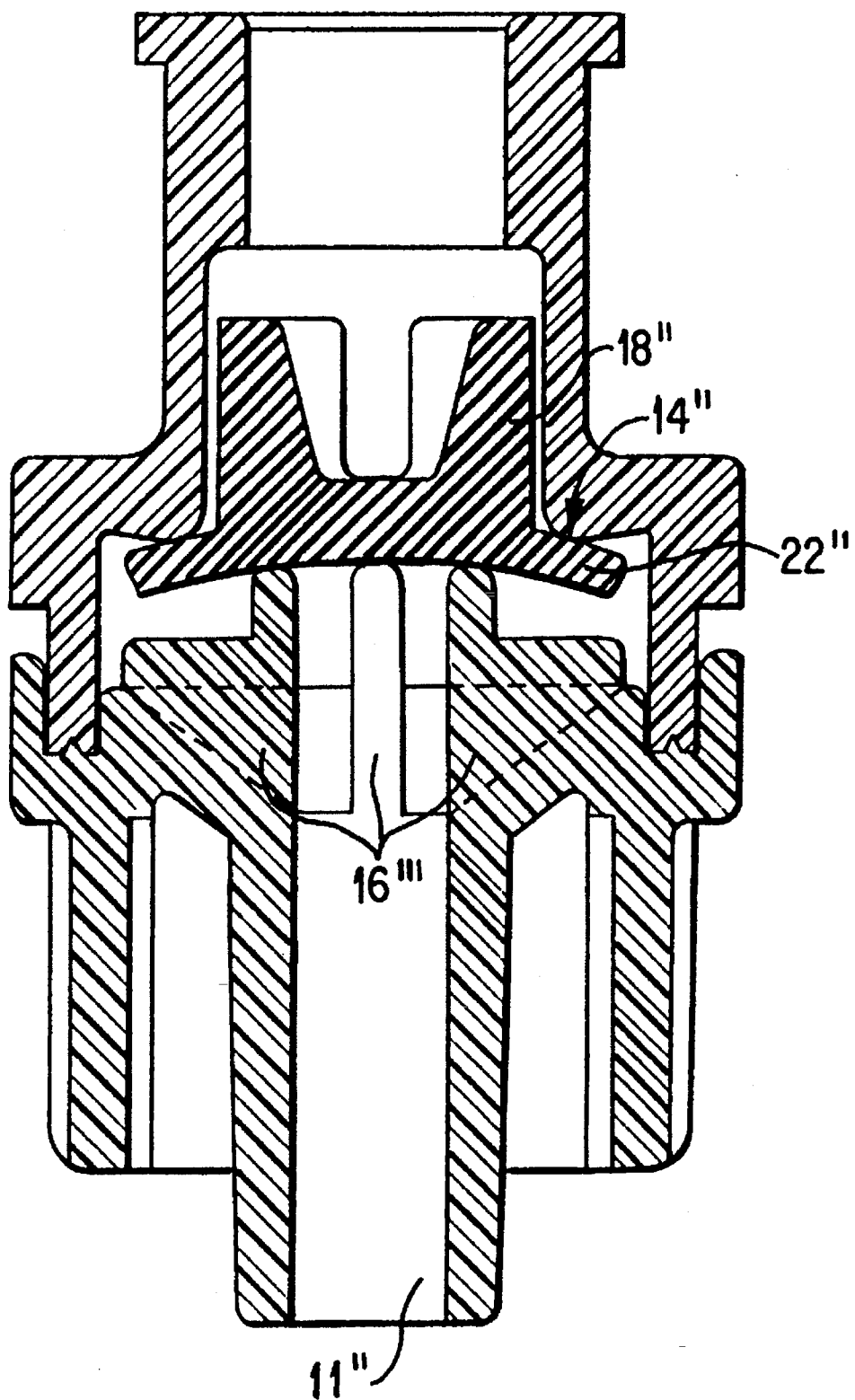
FIG. 4A shows a cross-sectional view of another alternative embodiment of the invention.
Figure 5:
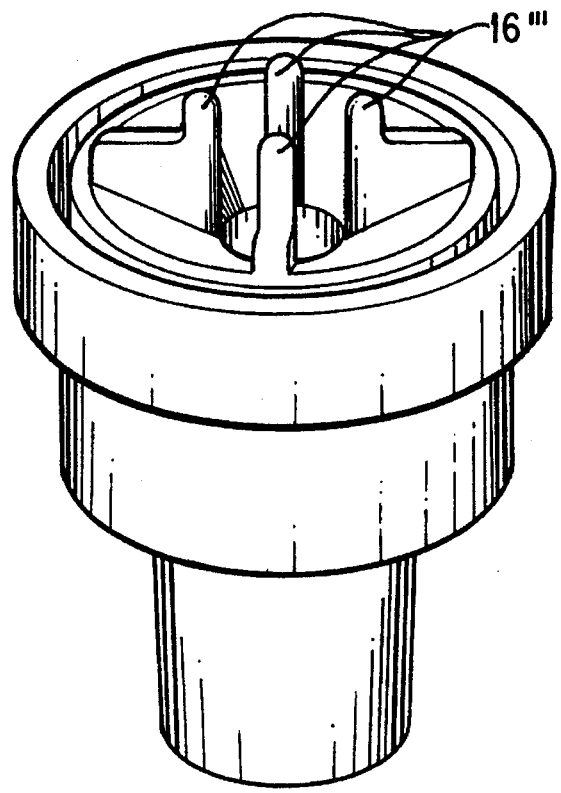
FIG. 5 shows a perspective view of a lower housing that may be used in a valve according to the present invention.
Figure 5A:
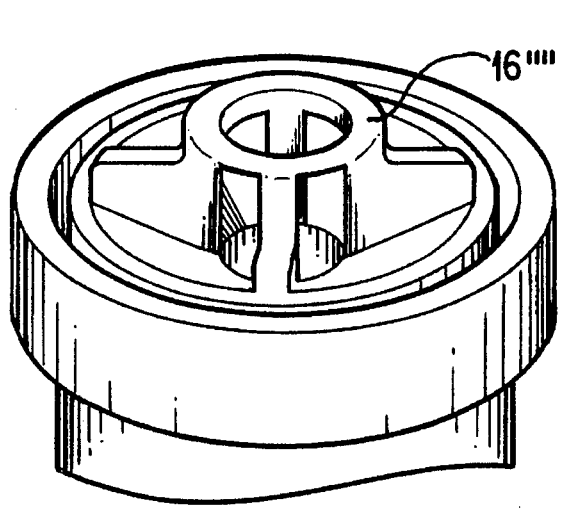
FIG. 5A shows a perspective view of the top portion of an alternative lower housing.
Figure 5B:
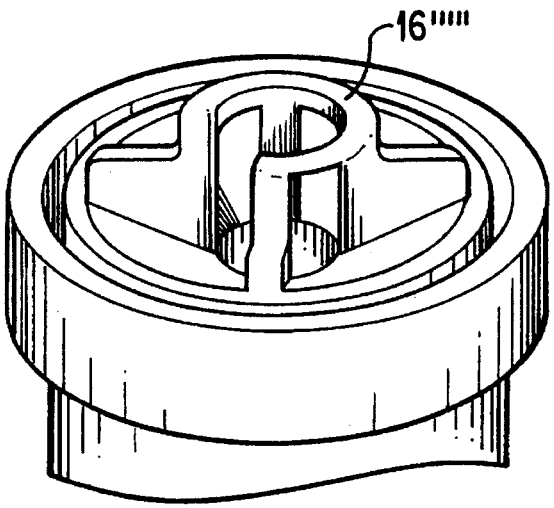
FIG. 5B shows a perspective view of the top portion of another alternative lower housing.

The buttress extension 16' shown in FIG. 4 is a single solid center prong. In useful embodiments allowing the insertion of needles or narrow blunt cannulas, the buttress extension 16' may be configured, as shown in FIGS. 4A and 5, as multiple prongs 16 (for example, four) spaced from the central axis or as a complete ring 16'' in FIG. 5A or broken ring 16'' in FIG. 5B spaced radially inward of the valve seat 14" FIG. 4A. These configurations would support the center region of valve element 18", but allow insertion of a needle or narrow blunt cannula respectively through a thin or slit center of valve element 18" and allow communication of fluid from the center of the outlet side of valve element 18" to outlet channel 11". Such buttress configurations make it less likely for flange portion 22" to separate from valve seat 14" in response to the force of insertion of a needle or blunt cannula. They also may provide a lateral buttress in the case of a slit opened by the insertion of a blunt cannula to provide compression to seal the slit material around the cannula to prevent fluid flow around the cannula. Modified versions of such buttress configurations 16" may also be used to similar advantage for the valve element 18" with an extended base, as shown in FIG. 1B".

It can be seen from these examples that a variety of different valve configurations can be constructed using the advantages of the invention herein.

We claim:

1. A flow control device comprising
   (a) a housing with internal walls defining a channel for the flow of fluid, with a step change from a first region with a first diameter to a second region with a second, larger diameter, providing a valve seat at said step change, and providing at least one buttress in said second region axially spaced from said valve seat; and
   (b) a single-piece valve element of resilient material comprising (i) a disk of a diameter greater than said first diameter and less than said second diameter; and (ii) an annular extension extending axially from one face with an outside diameter less than said first diameter defining an annular flange portion of said disk extending radially therefrom and an inner region adapted to engage resiliently a luer tip of diameter smaller than said first diameter; said valve element situated in said channel with said first annular extension situated within said first region of said channel, with said flange portion of said disk seated against said valve seat and a central portion of said disk, concentric with and of smaller diameter than said disk, opposite said annular extension engaging a portion of said buttress leaving free to move axially within said second region of said channel from said valve seat the portion of said flange radially outward from said central portion, thereby providing fluid communication between said first region and said second region.

2. Apparatus as defined in claim 1 wherein said buttress is provided in said second region of said channel extending at a point radially inward of said first diameter axially in the direction of said first region more than at the radially outward portions of said buttress to provide said portion for engaging said central portion of said disk.

3. Apparatus as defined in claim 1 wherein said disk further comprises a second annular extension extending substantially axially from the face of said disk opposite said first annular extension with a maximum outside diameter less than said second diameter such that said second annular extension provides said portion of said disk engaging said buttress.

4. A flow control device comprising
   (a) a housing with internal walls defining a channel for the flow of fluid, with a step change from a first region with a first diameter to a second region with a second, larger diameter, providing a valve seat at said step change, and providing at least one buttress in said second region axially spaced from said valve seat; and
   (b) a single-piece valve element of resilient material comprising (i) a disk of a diameter greater than said first diameter and less than said second diameter; (ii) an annular extension extending axially from one face with an outside diameter less than said first diameter defining an annular flange portion of said disk extending radially therefrom and an inner region adapted to engage resiliently a luer tip of diameter smaller than said first diameter; and (iii) a second annular extension extending substantially axially from the opposite face with a maximum outside diameter less than said second diameter; said valve element situated in said channel with said first annular extension situated within said first region of said channel, with said flange portion of said disk seated against said valve seat and said second annular extension pressed against said buttress, said flange portion axially separable from said valve seat upon sufficient pressure upon said first annular extension to allow fluid to communicate from said first region to said second region.

5. Apparatus as defined in claim 4 wherein said first annular extension is in the form of a hollow cylinder with axial slots.

6. Apparatus as defined in claim 4 wherein said first annular extension is hollow with an internally tapered wall.

7. Apparatus as defined in claim 6 wherein the internally tapered wall comprises a bevel at the end distal from said disk portion.

8. Apparatus as defined in claim 6 wherein the internally tapered wall comprises bevels alternating with radially inward projections at the end distal from said disk portion.

9. Apparatus as defined in claim 4 wherein said second annular extension is in the form of a hollow cylinder.

10. Apparatus as defined in claim 4 wherein said second annular extension is in the form of a hollow frustum of a cone.

11. Apparatus as defined in claim 4 wherein said valve element is composed of materials of different resilience molded in one piece.

12. Apparatus as defined in claim 4 wherein said buttresses are spaced away from the central axis of the apparatus.

13. Apparatus as defined in claim 4 wherein said valve element has a depression in the center of said disk within said first annular extension for guiding insertion of a needle or cannula.

14. Apparatus as defined in claim 4 wherein said valve element is perforated at the central axis of the valve element.

15. Apparatus as defined in claim 14 comprising a third extension from said disk immediately surrounding said perforation and engaging said buttresses to allow insertion of a cannula through said perforation without displacing said flange surface from said valve seat.

16. Apparatus as defined in claim 4 comprising a plurality of buttresses in said second region each extending at a point radially inward of said first diameter axially in the direction of said first region more than at the radially outward portions of said buttress.

17. Apparatus as defined in claim 4 wherein the buttress is in a form such that it extends axially in the direction of said first region more along an arc centered on the central axis of said channel than at other portions of said buttress.

18. Apparatus as defined in claim 4 wherein the buttress is in a form such that it extends axially in the direction of said first region more along a ting centered on the central axis of said channel than at other portions of said buttress.

19. A flow control device comprising
   (a) a housing with internal walls defining a channel for the flow of fluid, with a step change from a first region with a first diameter to a second region with a second, larger diameter, providing a valve seat at said step change, and providing at least one buttress in said second region extending at a point radially inward of said first diameter axially in the direction of said first region more than at the radially outward portions of said buttress; and (b) a single-piece valve element of resilient material comprising (i) a disk of a diameter greater than said first diameter and less than said second diameter; and (ii) an annular extension extending axially from one face with an outside diameter less than said first diameter defining an annular flange surface of said disk extending radially therefrom; said valve element situated in said channel with said annular extension situated within said first region of said channel, with said flange surface of said disk seated against said valve seat and a central portion of said disk opposite said annular extension engaging said extension of said buttress leaving tree to move axially within said second region of said channel from said valve sat the radially outward portion of said flange.

20. Apparatus as defined in claim 19 wherein said annular extension is in the form of a hollow cylinder with axial slots.

21. Apparatus as defined in claim 19 wherein said first annular extension is hollow with an internally tapered wall.

22. Apparatus as defined in claim 21 wherein the internally tapered wall comprises a bevel at the end distal from said disk portion.

23. Apparatus as defined in claim 21 wherein the internally tapered wall comprises bevels alternating with radially inward projections at the end distal from said disk portion.

24. Apparatus as defined in claim 19 wherein said valve element is composed of materials of different resilience molded in one piece.

25. Apparatus as defined in claim 19 wherein said extension of said buttress is at a point on the central axis of said channel.

26. Apparatus as defined in claim 19 comprising a plurality of buttresses in said second region each extending at a point radially inward of said first diameter axially in the direction of said first region more than at the radially outward portions of said buttress.

27. Apparatus as defined in claim 26 wherein said plurality of buttresses are in the form of four prongs evenly distributed along a ring centered on the central axis of said channel.

28. Apparatus as defined in claim 19 wherein the buttress is in a form such that it engages said central portion of said disk in an arc centered on the central axis of said channel.

29. Apparatus as defined in claim 19 wherein the buttress is in a form such that it engages said central portion of said disk in a ring centered on the central axis of said channel.

30. Apparatus as defined in claim 19 wherein said valve element has a depression in the center of said disk within said annular extension for guiding insertion of a needle or cannula.

* * * * *

UNITED STATES PATENT AND TRADEMARK OFFICE
CERTIFICATE OF CORRECTION

PATENT NO. : 5,535,785
DATED : July 16, 1996
INVENTOR(S) : Robert W. Werge, et al It is certified that error appears in the above-indentified patent and that said Letters Patent is hereby corrected as shown below:

Col. 6, line 63, change "ting" to --ring--.
Col. 7, line 19, change "tree" to --free--.
Col. 7, line 21, change "sat" to --seat--.

Signed and Sealed this

Fifth Day of November, 1996

Attest:

BRUCE LEHMAN

Attesting Officer — Commissioner of Patents and Trademarks